US009833299B2

(12) United States Patent
Shotton et al.

(10) Patent No.: US 9,833,299 B2
(45) Date of Patent: Dec. 5, 2017

(54) MULTI-DIRECTIONAL HANDPIECE

(71) Applicant: DENTSPLY International Inc., York, PA (US)

(72) Inventors: Vincent Shotton, Broken Arrow, OK (US); Dan Ammon, Tulsa, OK (US); Naim Karazivan, Repentigny (CA)

(73) Assignee: DENTSPLY International Inc., York, PA (US)

( * ) Notice: Subject to any disclaimer, the term of this patent is extended or adjusted under 35 U.S.C. 154(b) by 60 days.

(21) Appl. No.: 14/566,668

(22) Filed: Dec. 10, 2014

(65) Prior Publication Data

US 2015/0164614 A1 Jun. 18, 2015

Related U.S. Application Data

(60) Provisional application No. 61/913,947, filed on Dec. 10, 2013.

(51) Int. Cl.

| *A61C 1/14* | (2006.01) |
|---|---|
| *A61C 1/02* | (2006.01) |
| *A61C 1/12* | (2006.01) |
| *A61C 1/18* | (2006.01) |
| *A61C 1/00* | (2006.01) |
| *A61C 1/07* | (2006.01) |
| *A61C 5/40* | (2017.01) |
| *A61C 5/42* | (2017.01) |

(52) U.S. Cl.
CPC .............. *A61C 1/148* (2013.01); *A61C 1/003* (2013.01); *A61C 1/02* (2013.01); *A61C 1/07* (2013.01); *A61C 1/12* (2013.01); *A61C 1/185* (2013.01); *A61C 5/40* (2017.02); *A61C 5/42* (2017.02)

(58) Field of Classification Search
CPC ...................................................... A61C 1/148
See application file for complete search history.

(56) References Cited

U.S. PATENT DOCUMENTS

| 5,145,369 A | * | 9/1992 | Lustig | .................... A61C 17/00 |
|---|---|---|---|---|
| | | | | 433/118 |
| 2010/0268235 A1 | * | 10/2010 | Teichmann | ........ A61B 17/1655 |
| | | | | 606/80 |
| 2013/0101958 A1 | * | 4/2013 | Garcia | ..................... A61C 1/06 |
| | | | | 433/122 |

FOREIGN PATENT DOCUMENTS

EP          1078606          *   2/2001   ............... A61C 1/12

* cited by examiner

*Primary Examiner* — Eric D. Bertram
(74) *Attorney, Agent, or Firm* — David A. Zdurne; Douglas J. Hura; Leana Levin

(57) ABSTRACT

A multi-directional handpiece that includes a motor drive extending along and configured for rotation about a body axis, the motor drive having: a motor gearing at a proximal end of the motor drive; and a file gearing in engagement with the motor gearing for transferring the rotational and axial movement to a workpiece; and a housing for the workpiece; and wherein through rotation of the motor drive, the workpiece moves in an axial oscillating motion while being rotated.

9 Claims, 8 Drawing Sheets

MULTI-DIRECTIONAL HANDPIECE

RELATED APPLICATIONS

This patent application claims the benefit of and priority to U.S. Provisional Patent Application Ser. No. 61/913,947, filed on Dec. 10, 2013, which is herein incorporated by reference for all purposes.

FIELD OF INVENTION

The present invention relates to endodontic instruments, and more particularly, rotating, reciprocating, and/or oscillating instruments.

BACKGROUND OF THE INVENTION

Current contra angle handpieces are designed either to only rotate the file or to move the file up and down without rotating it. Each motion has its own separate advantages. By rotating the file, due to the file fluting, this allows the file to engage with the root canal and clean and shape more efficiently. The disadvantage to pure rotation movement is the susceptibility to over torque the file while performing a root canal procedure. If the file begins to bind in the canal, it can increase the potential for the file to either unwind or separate. Also, by having pure rotation, if the file is going around a curve and is held at that curve too long, cyclical fatigue can cause the file to separate. By having only an up and down motion without any rotation of the file, it prevents the file from over torque. It also prevents the file from experiencing cyclical fatigue failure due to extensive rotational motion while going around a curve. The disadvantage of just up and down motion is that the cutting efficiency is significantly reduced due to the design of the file and its fluting.

There are many commercially available contra angle handpieces that have the capability of rotating the file clockwise, counterclockwise, or in reciprocation motions when connected to an endodontic motor (Aseptico, ATR, Sirona). These contra angle handpieces are available in many different gear ratios based upon the desired RPM capabilities of the clinician. Also, there are commercially available contra angle handpieces that have the capability of vertically oscillating the file in an up and down motion without rotation (EndoPulse, ReDent). U.S. Pat. No. 8,172,572 discusses a handpiece design that has a reciprocating motion parallel to the tool axis at a first frequency of oscillations per minute and rotates about the tool axis at a frequency at a second frequency of rotations per minute, wherein said first frequency is at least one order of magnitude greater than said second frequency. It goes on to state that the tool holder rotates through a rotational step of no more than a fortieth of a revolution about said tool axis. It also states that the first frequency (motion parallel to the tool axis) is at least two orders of magnitude greater than said second frequency (rotation about the tool axis). This type of design is primarily intended to vertically oscillate at a much greater magnitude than it rotates. By having this type of motion, most conventional rotary files would not be able to be used with this type of contra angle design because the rotation is not balanced with the vertical oscillation. Most conventional file designs would prefer no more than a ratio of 8 to 1 where there are 8 vertical oscillations for every rotation of the file. U.S. Pat. Nos. 4,175,324; 5,169,312; 5,454,718; and 5,453,008 discuss using an eccentric shaft or pin, which is driven by the motor to cause the file in the contra angle to move up and down. This is perfectly fine for a concept where the file is only moving in a vertical motion and not rotationally. The problem comes when the desire is for the file to rotate as well. Therefore, a separate component would have to be added to have the file rotate while driven by the motor. U.S. Pat. No. 5,145,369 discusses a cam mechanism where FIG. 60 is rotating along the top of the contra angle and a restoring spring is used to apply constant pressure to the cam mechanism thus allowing it to rotating while moving up and down. The key in this design is that the cam mechanism will generate friction if not lubricated well and may cause the cam mechanism to wear down over time depending on the spring constant of the restoring spring. U.S. Pat. Nos. 6,106,290 and 4,289,849 discusses a hand piece with groove portions or a L-shaped link arm which allows the file to reciprocate both vertically and in rotation. The problem with this design is that the file is never allowed to fully rotate 360° which will limit the cutting efficiency of the file as it progresses within the root canal.

Most current contra angle handpieces are designed either to only rotate the file or to oscillate the file up and down without rotating it. Each motion has its own separate advantages. By rotating the file, due to the file fluting, this allows the file to engage with the root canal and clean and shape more efficiently. The disadvantage to pure rotation movement is the susceptibility to over torque the file while performing a root canal procedure. If the file begins to bind in the canal, it can increase the potential for the file to either unwind or separate. Also with pure rotation, some file designs allow the file to screw into the canal thus causing the clinician to lose control of the progression of the file. This can lead to transportation or apical zipping of the canal. Also, by having pure rotation, if the file is going around a curve and is held at the curve too long, cyclical fatigue can cause the file to separate. By having only an up and down vertical motion without any rotation of the file, it prevents the file from over torque. It also prevents the file from experiencing cyclical fatigue failure due to extensive rotational motion while going around a curve. The disadvantage of just up and down motion is that the cutting efficiency is significantly reduced due to the design of the file and its fluting. By having a motion of the file that is both in rotation as well as axial movement up and down, it allows the file to clean and shape efficiently while reducing the torque and cyclical fatigue exposure on the file.

As such, the present invention attempts to overcome these problems by providing a handpiece configured to achieve a motion (e.g., a motion of a file) having both rotation (e.g., clockwise, counterclockwise, or a combination of both movement about the file axis) as well as oscillation (e.g., axial movement up and down) dual motion. This dual functionality allows the file to clean and shape efficiently while reducing the torque created on the file and cyclical fatigue exposure.

SUMMARY OF INVENTION

The present invention seeks to improve upon prior rotary instruments by providing improved multi-directional instruments. In one aspect, the present invention provides a multi-directional handpiece comprising: a motor drive extending along and configured for rotation about a body axis, the motor drive having: a motor gearing at a proximal end of the motor drive; and a file gearing in engagement with the motor gearing for transferring the rotational and axial movement to a workpiece; and a housing for the workpiece;

and wherein through rotation of the motor drive, the workpiece moves in an axial oscillating motion while being rotated.

In another aspect, the present invention contemplates a multi-directional handpiece comprising: a motor drive extending along and configured for rotation about a body axis, the motor drive having: a motor gearing at a proximal end of the motor drive; and a cam drive at the proximal end of the motor drive, the cam drive extending along an axis offset from the body axis; and a cam follower extending along a head axis; the cam follower having: a groove having opposing spaced apart walls for receiving the cam drive; a file gearing in engagement with the motor gearing for transferring the rotational movement of the motor drive about the body axis to the cam follower about the head axis; and a housing for a workpiece; and wherein through rotation of the motor drive, the cam drive revolves along a displaced path from the body axis thereby moving the cam follower generally along the head axis so that the workpiece moves in an oscillating motion while being rotated.

In another aspect, the present invention contemplates a multi-directional handpiece comprising: a fixed pin (e.g., stationary pin); a motor drive extending along and configured for rotation about a body axis, the motor drive having: a motor gearing at a proximal end of the motor drive; and a file drive extending along a head axis; the file drive having: a file gearing in engagement with the motor gearing for transferring the rotational movement of the motor drive about the body axis to the file drive about the head axis; and a follower member including a radial groove having opposing spaced apart walls, the walls including a plurality of sections (e.g., curves) having a first section being displaced axially relative to a second section along the head axis to define an offset path that is dimensioned for receiving the fixed pin; and a housing for a workpiece; and wherein as the file drive rotates, at least one wall of the radial groove is rotated towards the fixed pin so that upon contact with the fixed pin, the follower member is axially displaced generally along the head axis so that the workpiece moves in an oscillating motion while being rotated.

In yet another aspect, any of the aspects of the present invention may be further characterized by one or any combination of the following features: wherein the workpiece is axially oscillated from 1 to 20 times for every revolution; wherein the workpiece is axially oscillated from 1 to 10 times for every revolution; wherein the workpiece is axially oscillated at least 1 time for every revolution; wherein the workpiece is axially oscillated at least 2 times for every revolution; wherein the workpiece is axially oscillated less than 10 times for every revolution; wherein the workpiece is axially oscillated less than 7 times for every revolution; wherein the motor drive includes a cam drive at the proximal end of the motor drive, the cam drive extending along an axis offset from the body axis; wherein the cam follower extends along a head axis having a groove with opposing space apart walls for receiving the cam drive; wherein the workpiece is rotated either clockwise, counterclockwise or in reciprocation; wherein the workpiece/tool is a file; or any combination thereof.

It should be appreciated that the above referenced aspects and examples are non-limiting as others exist with the present invention, as shown and described herein. For example, any of the above mentioned aspects or features of the invention may be combined to form other unique configurations, as described herein, demonstrated in the drawings, or otherwise.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
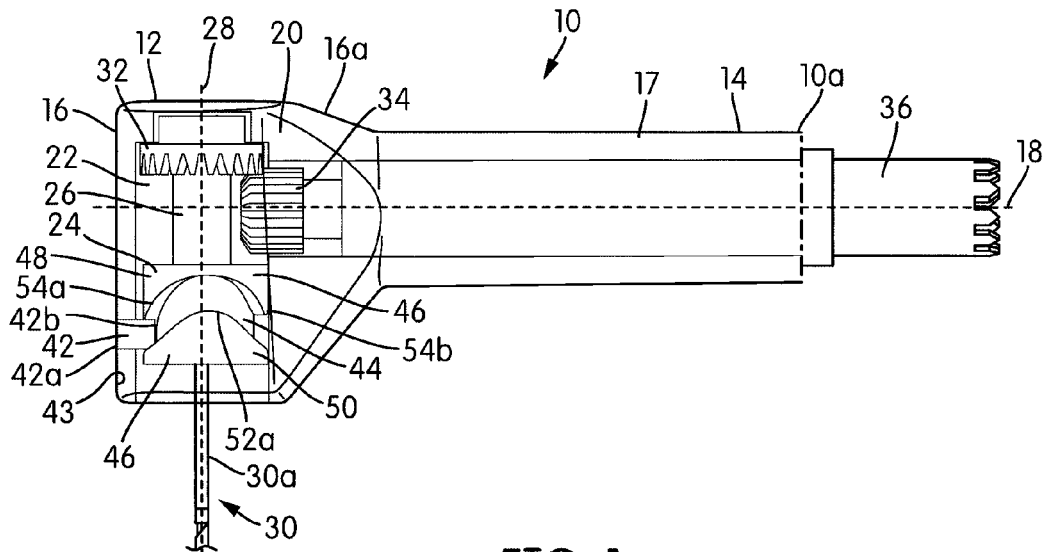
FIG. 1 is a side view of a portion of a multi-directional handpiece assembly in a first position in accordance with embodiments of the present invention.

The present invention may provide a multi-directional handpiece. More particularly, the present invention may provide a rotary file handpiece (contra angle) for simultaneously rotating (either clockwise, counterclockwise, or reciprocating clockwise and counterclockwise) and oscillating (moving up and down in an axial reciprocating movement) an endodontic file attached thereto. It is appreciated that the multi-directional handpieces of the present invention may simultaneously rotate and move axially the rotary file for cleaning and shaping a root canal.

Desirably the file may rotate either clockwise, counterclockwise, or in reciprocation (e.g., intermittent rotation between counterclockwise rotation and clockwise rotation) while simultaneously oscillating vertically up and down (e.g., above and below the Handpiece Body Axis). The multi-directional handpiece may be configured so that the workpiece (e.g., file) axially oscillates at least 1, preferably at least 2, and more preferably at least 3 times or more (e.g., 5, 6, or 7 times) for every revolution (e.g., rotation such as clockwise, counterclockwise, or in reciprocation). Furthermore it is appreciated that the workpiece may be axially oscillated less than 20, preferably less than 15, and more preferably less than 10 (e.g., 7) times for every revolution. For example, the workpiece may be axially oscillated from 1 to 20, preferably from 2 to 15, and more preferably from 3 to 10 (e.g., from 3 to 7) times for every revolution. As referred to herein, an oscillation may be describe as one cycle from a first position to a second position and returning to the first position.

It is believed that one advantage to having a simultaneous rotation and vertical oscillation motion for the endodontic file may be that it allows the file to clean and shape efficiently while reducing the torque and cyclical fatigue exposure that the file sees in traditional rotary only motions.

In the present exemplary embodiment, the multi-directional handpiece 10 comprises a handpiece head 12 and only part of a handpiece body 14. The handpiece head 12 includes an angular head housing 16 whose rear body housing section 17, when mounted to the handpiece 10, is a forward extension of the gripping sleeve 10a of the handpiece 10 having a longitudinal axis 18.

Figure 2:
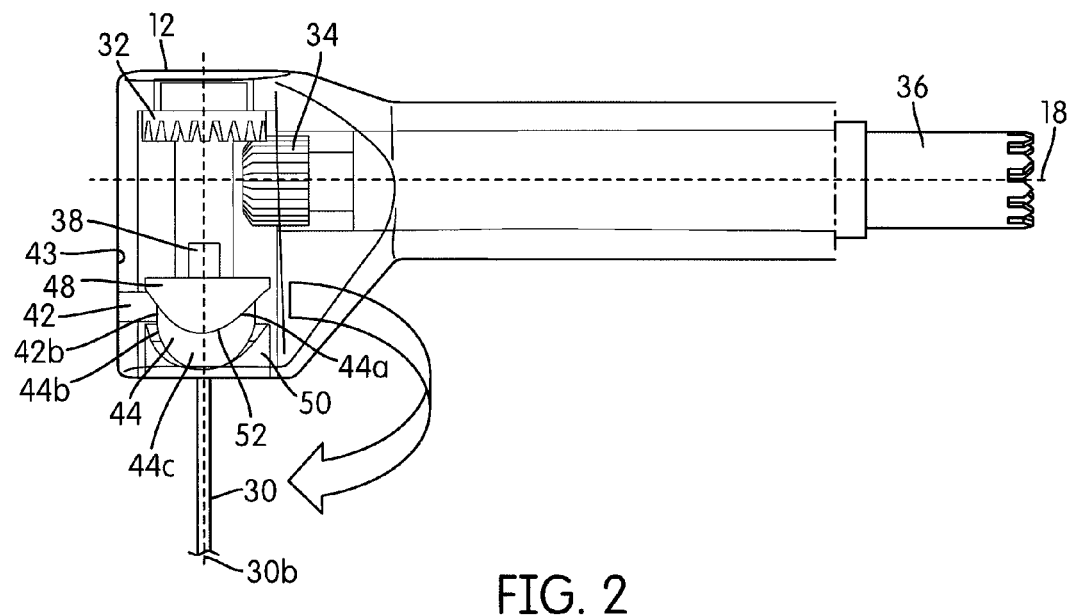
FIG. 2 is a side view of the portion of the multi-directional handpiece assembly in a second position in accordance with embodiments of the present invention.
Figure 3:
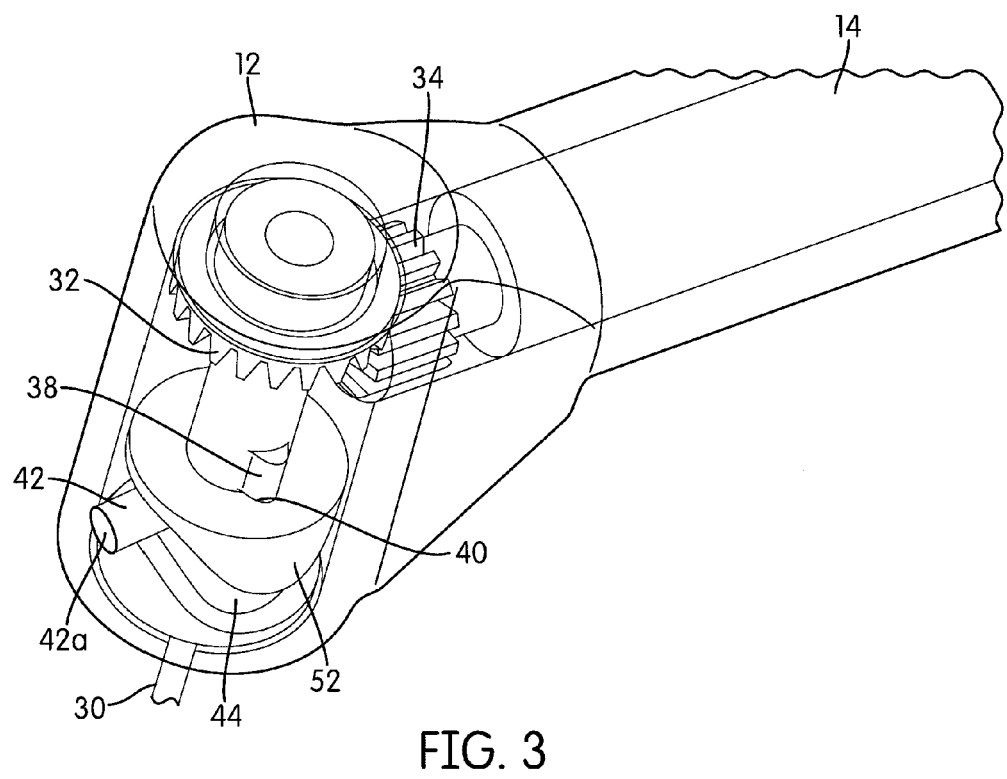
FIG. 3 is a zoomed in perspective view of the portion of the multi-directional handpiece assembly shown in FIG. 2.

As shown in particular in FIGS. 1-3 the angular head housing 16 has in the region of its head housing section 16a an axial bearing bore 20 which leads forward into a continuous bearing bore 22 that extends at right angles thereto and is manufactured with steps. In the bearing bore 22, a following member 24 is mounted to a tool drive 26 so that it can move up and down in its longitudinal direction (along the head axis 28), i.e. transverse to the handpiece body 14, and rotate (about the head axis 28). In the cylindrical bore (not shown) of the following member 24 there is a treatment tool 30 (e.g., workpiece or file such as an endodontic file) having a cylindrical holding shaft 30a arranged along its axis 30b, which can be inserted slidingly from the tool side and clamped. The tool 30 operates by oscillating longitudinally (e.g., up and down along head axis 28).

The tool drive 26 has in its upper region a tool gearing 32, which is capable of rotating the tool drive 26 about the head axis 28. The tool gearing 32 is spaced axially from the follow member 24 to provide space for a motor gearing 34, which extends from a motor drive 36. The motor drive 36 transfers power from the motor (not shown) in a rotational movement about the body axis 18. The motor gearing 36 translates the rotational drive power (e.g., rotational movement about the body axis 18) from the motor drive 36 through the tool gearing 32 to provide rotational drive power (e.g., rotational movement about the head axis 28) along the tool drive 26.

In one specific example, the tool drive 26 includes at least one longitudinal rib 38 (preferably two opposing spaced ribs) for receiving and guiding the following member 24 by way the at least one corresponding longitudinal groove 40 (preferably two opposing spaced grooves). It is appreciated that this is only one example and should not be limited to this specific orientation. For example, the at least one longitudinal rib 38 may be located on the following 24 while the respective at least one longitudinal groove 40 may be provided on the tool drive 26. It is appreciated that slidable movement of the following member 24 in cooperation with the tool drive 26 may be accomplished by other means known in the art.

The longitudinal ribs 38 mate with the longitudinal grooves 40, respectively, and allows for slidable movement of the following member 24 along the head axis 28, which results in the oscillating motion of the tool 30. The length of the longitudinal rib 38 and/or the longitudinal groove 40 should be sufficient to allow the following member 24 the maximum movement (e.g., vertical height/depth of oscillation of the tool 30) depending on the shape/size of the following member 24.

The head 12 may further included a fixable pin 42 extending from an internal surface 43 of the head housing 16. The fixable pin 42 may be in a fixed (e.g., stationary) location or may be movable between two or more fixed locations/positions (e.g., in a generally parallel direction to the head axis 28). The fixable pin 42 may include a fixed end 42a and a free end 42b generally extending in a transverse direction to the head axis 28. The free end 42b of the fixable pin 42 extends into an outer groove 44 of the following member 24.

The following member 24 may include an outer surface 46, which includes an upper portion 48 and a lower portion 50 defined by the outer groove 44, therebetween. The outer groove 44 may include a top wall 44a, a bottom wall 44b, and a base surface 44c extending therebetween. It is appreciated that the outer groove 44 may extend along at least portion of or preferably entirely around the following member 24 (in a generally transverse direction to the head axis 28).

The outer groove 44 may define a generally sinusoidal path, though not required. Other path shapes are contemplated. Preferably, the outer groove 44 includes one or more displacement portions 52 (e.g., one or more pairs of displacement portions) having at least a first pair of corresponding displacement portions. In one specific embodiment, as shown if FIGS. 1-3, the outer groove 44 may include a first pair of corresponding displacement portions 52a and 52b and a second pair of corresponding displacement portions 54a and 54b. In this specific example, the pair of corresponding displacement portions 52a and 52b are located on opposing sides of the following member 24 while the second pair of corresponding displacement portions 54a and 54b are also located on different opposing sides of the following member 24. Preferably, the displacement portions may be equally spaced from one another, though not required.

Figure 4:
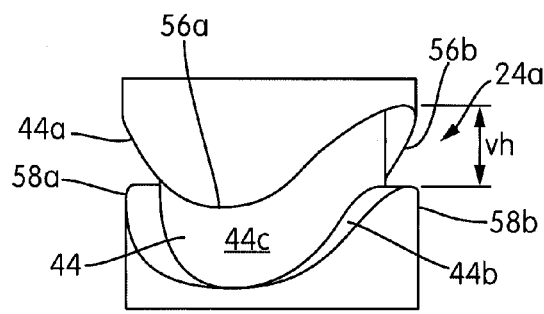
FIG. 4 is a side view of an alternative following member of another multi-directional handpiece assembly in accordance with embodiments of the present invention.
Figure 5:
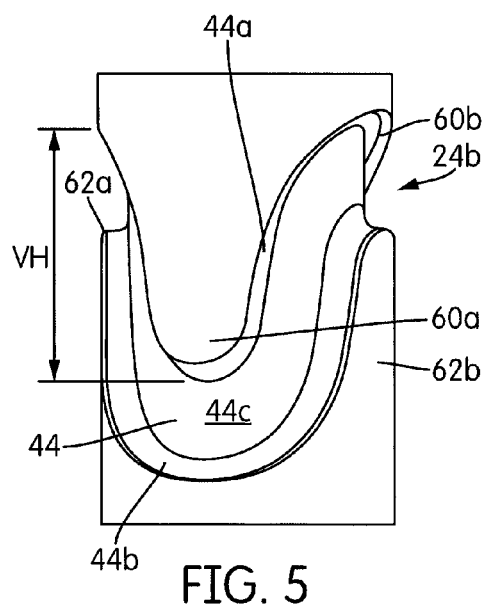
FIG. 5 is a side view of another alternative following member of another multi-directional handpiece assembly in accordance with embodiments of the present invention.
Figure 6:
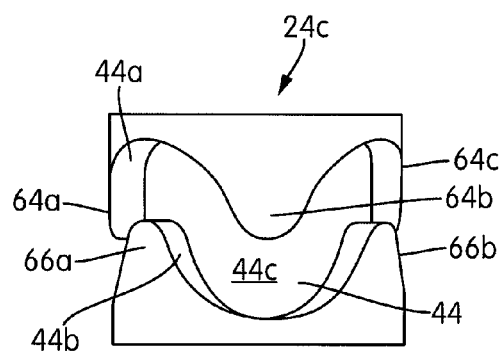
FIG. 6 is a side view of another alternative following member of another multi-directional handpiece assembly in accordance with embodiments of the present invention.
Figure 7:
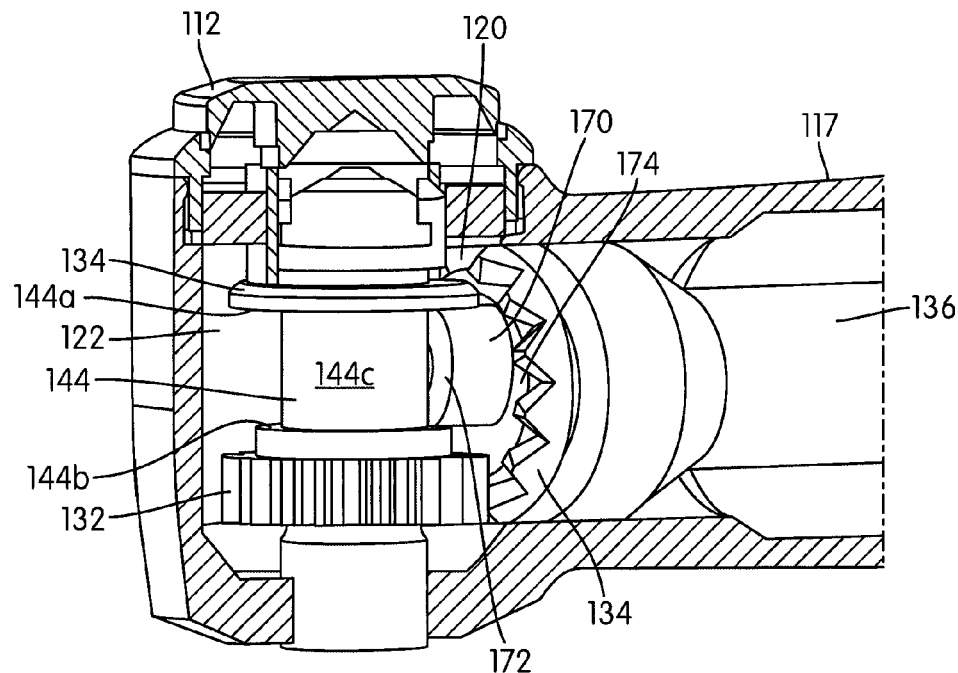
FIG. 7 is a perspective view of a portion of another multi-directional handpiece assembly in a first position in accordance with embodiments of the present invention.
Figure 8:
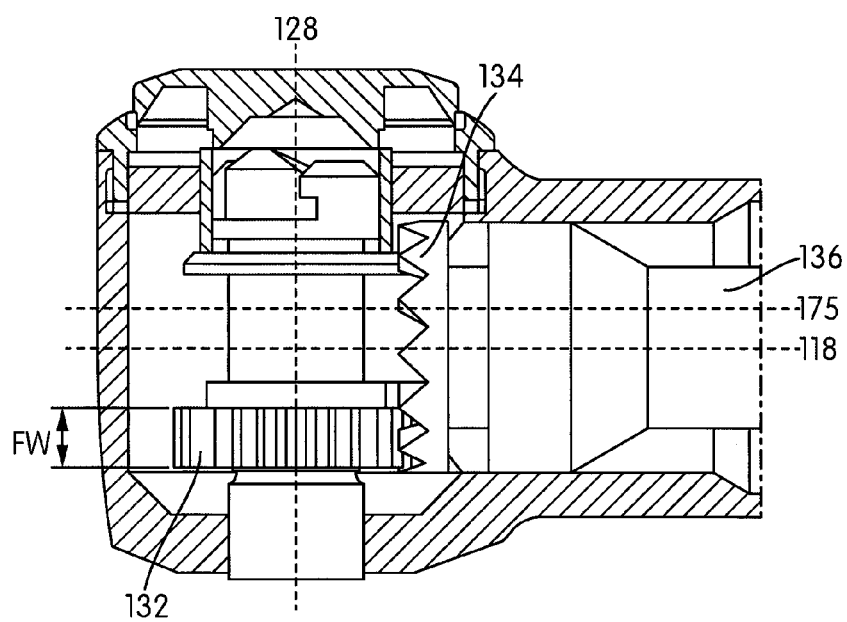
FIG. 8 is a side view of the another multi-directional handpiece assembly shown in FIG. 7.
Figure 9:
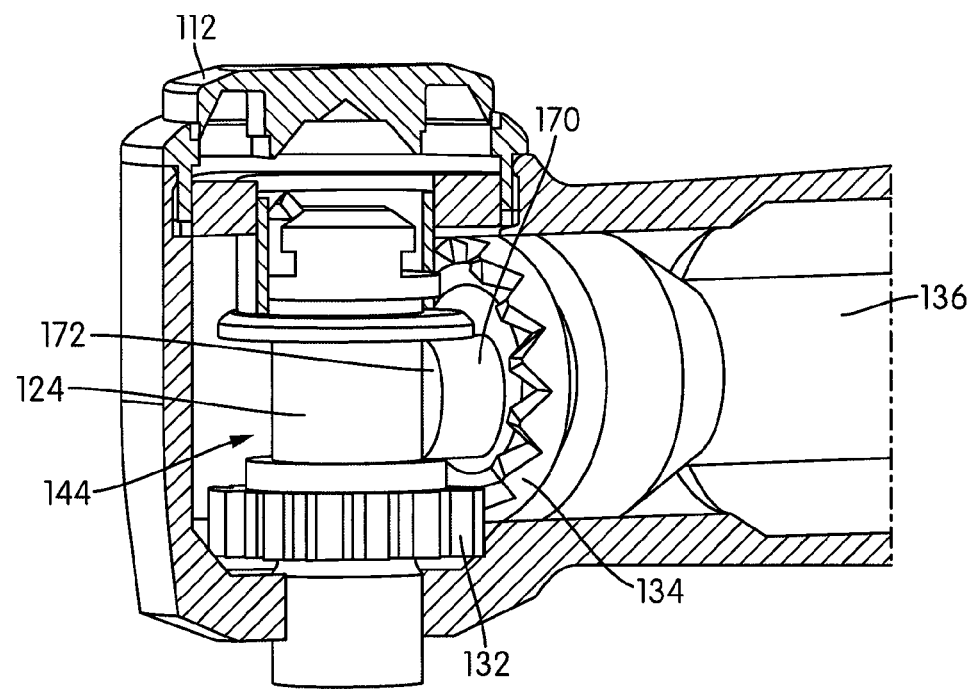
FIG. 9 is a perspective view of the portion of the another multi-directional handpiece assembly in a second position in accordance with embodiments of the present invention.
Figure 10:
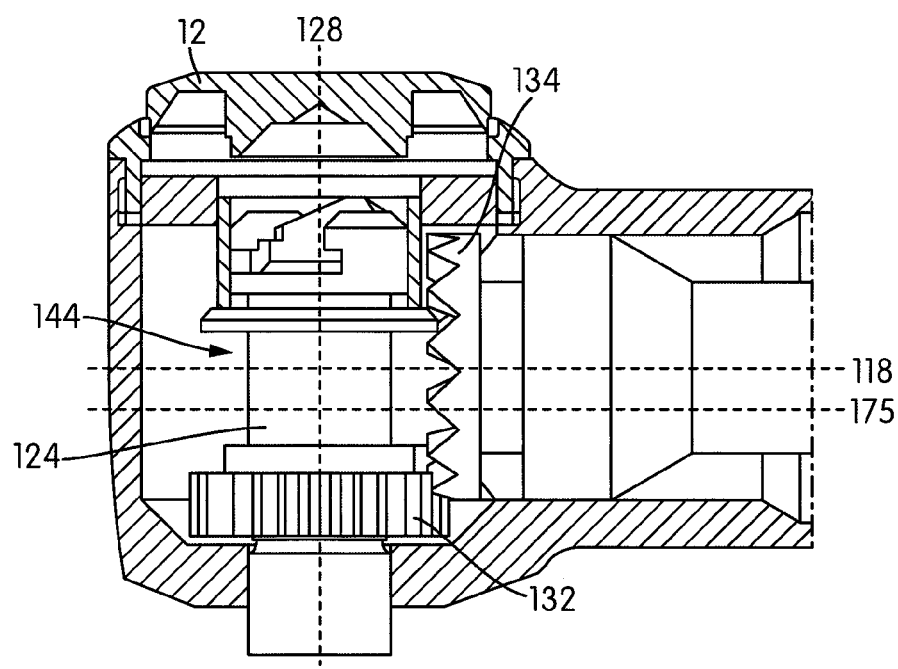
FIG. 10 is a side view of the another multi-directional handpiece assembly shown in FIG. 9.
Figure 11A:
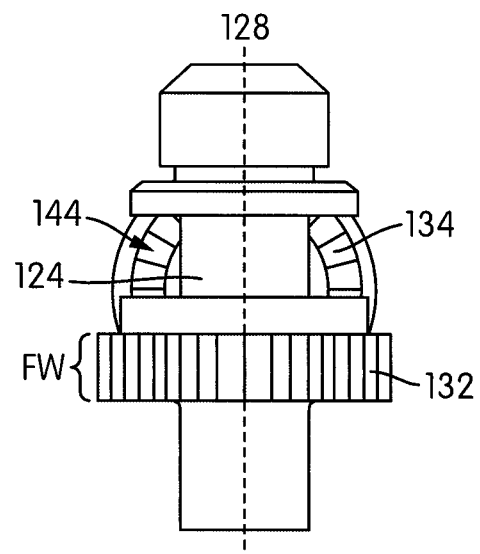
FIG. 11A is a front view of the multi-directional handpiece shown in FIG. 8 without the headpiece housing showing the cam follower in a first vertical position.
Figure 11B:
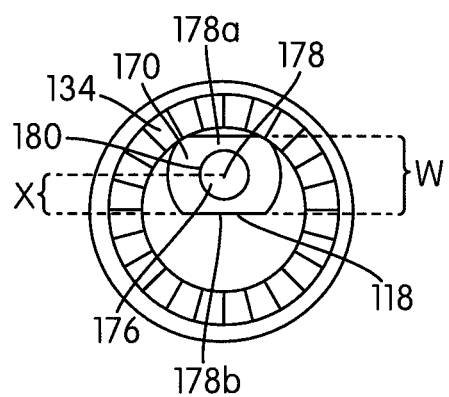
FIG. 11B is a front view of the multi-directional handpiece shown in FIG. 11A without the cam follower.
Figure 12A:
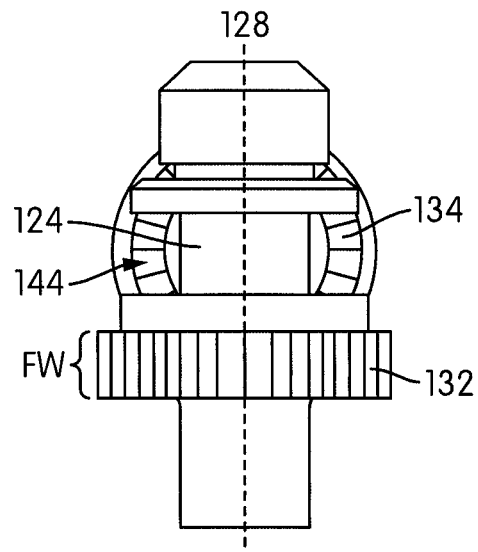
FIG. 12A is a front view of the multi-directional handpiece shown in FIG. 8 without the headpiece housing showing the cam follower in a second vertical position.
Figure 12B:
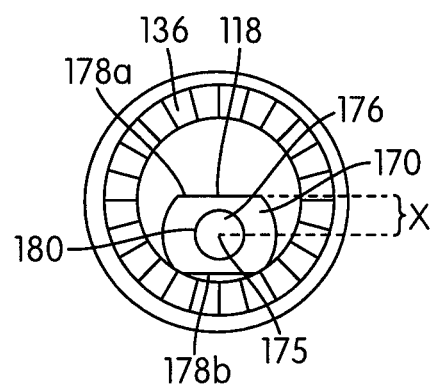
FIG. 12B is a front view of the multi-directional handpiece shown in FIG. 11A without the cam follower.

Optionally, the following member 24 may be provided in alternative shapes/sizes 24a, 24b, and 24c (FIGS. 4-6) and/or may be removable to accommodate these alternative following members in one or more multi-directional handpieces 12. These alternative following members may be designed to accommodate various preferences in desired vertical oscillation height/depth (e.g., about 0.5 mm to about 4.5 mm, preferably about 1 mm to about 3 mm) and/or number of oscillations per rotation (e.g., 1 to 20, typically 1 to 10, and preferably 2 to 4) of the tool into a working area (e.g., root canal).

It is appreciated that height of each pair of corresponding displacement portions and the number of pairs of corresponding displacement portions define vertical oscillation height and the number of oscillations per rotation, respectively. For example, the pairs of corresponding displacement portions 56a,56b and 58a,58b in FIG. 4 have a smaller vertical height "vh" than a larger vertical height "VH" of the pairs of corresponding displacement portions 60a,60b and 62a,62b in FIG. 5. Furthermore, for example, FIGS. 4-5 include four pairs of corresponding displacement portions 56a,56b, 58a,58b, 60a,60b and 62a,62b, which result in two full vertical oscillations for every one rotation of the tool as compared to FIG. 6, which includes six pairs of corresponding displacement portions 64a, 64b, 64c and 66a, 66b, 66c (not shown) resulting in three full vertical oscillation for every one rotation of the tool.

It is appreciated that the simultaneous movement (e.g., rotation and oscillation) may be achieved through rotation of the motor drive 36 by way of the motor so that the gearing from the motor drive 36 engages the gearing of the tool drive 26, which then causes the tool drive 26 to rotate. As the tool drive 26 rotates, the ribs 38 in the tool drive 26 engage with the grooves 40 in the follower member 24 thus causing the follower member 24 to rotate. As the follower member rotates 24, the outer groove 44 that may be peripherally located around the follower member 24 engages with the fixable pin 42 (while in a fixed position) causing the follower member 24 to oscillate vertically in an up and down manner as it is rotating. The tool 30 is connected to the follower member 24, which then causes the tool 30 to rotate as it is vertically oscillating in an up and down manner.

More particularly in use, it is appreciated that as the tool drive 26 rotates the following member 24 about the head axis 28, at least one of the top surface 44a and/or the bottom surface 44b of at least one of the displacement portions 52 engages the fixable pin 42 (e.g., in a fixed position) thereby displacing the following member 24 along the longitudinal rib 38. During rotation of the tool drive 26, the fixable pin 42 continues to engage various displacement portions 52 along the outer groove 44 such that the following member 24 (and the tool 30) moves in the vertical direction (e.g., up or down along the head axis) corresponding the vertical height of each respective displacement portion 52. This oscillating movement may continue until the rotation of the tool drive 26 ceases.

Optionally, in another embodiment, the fixable pin 42 may be moved to a non-fixed position (while optionally fixing the following member 24 at one vertical height position) so that as the following member 24 rotates the fixable pin 42 is movable in a vertical direction (e.g., up or down in the direction parallel to head axis 28) along the inner surface 43 of the head housing. In doing so, the displacement portions 52 engage the free end 42b of the fixable pin 42 thereby displacing the fixable pin 42 vertically while allowing the following member 24 to freely rotate without oscillation, though not required.

In another optional embodiment, the fixable pin 42 may be moved to a different fixed position along the head housing 16 (e.g., up or down relative to the exemplary position shown in FIGS. 1-3 in the direction parallel to head axis 28) to increase or decrease the depth of the tool oscillation into a work area (e.g., such as a root canal) relative to the predetermined vertical height of the one or more displacement portions 52.

The present invention further contemplates alternate embodiments of the multi-directional handpiece. For example, the outer groove 44 in the follower member 24 may be modified to adjust the number of vertical oscillations per every rotation of the tool or the amount (e.g., the distance) of vertical displacement desired, and/or a combination of both.

FIGS. 7-12B illustrate another alternate embodiment of the present invention, which may include a multi-directional handpiece 110 having a handpiece head portion 112 and a generally longitudinal handpiece body 114. The head portion 112 extending generally transversely from the body 114 and includes a handpiece housing 116 whose rear body housing section 117, when mounted to the handpiece 110, is a forward extension of the gripping sleeve (not shown) of the handpiece 110 having a longitudinal axis 118.

The angular head housing 116 has in the region of its head housing section 116a an axial bearing bore 120 which leads forward into a continuous bearing bore 122 that extends at right angles thereto. In the bearing bore 122, a cam follower 124 is provided so that it can move up and down in its longitudinal direction (along the head axis 128), i.e. transverse to the handpiece body 114, and rotate about the head axis 28. In the cylindrical bore (not shown) of the cam follower 124 there is a treatment tool (not shown, e.g., file such as an endodontic file) having a cylindrical holding shaft arranged along its axis similar to what is shown in FIGS. 1-3, which can be inserted slidingly from the tool side and clamped. The cam follower 124 has in its lower region a tool gearing 132, which is capable of rotating the cam follower 124 about the head axis 128.

Desirably, the multi-directional handpiece 110 may be configured to rotate the file either clockwise, counterclockwise, or in reciprocation while simultaneously oscillating the file vertically up and down. This multi-directional movement may be achieved through a motor drive 136, which is being rotated by a motor (not shown) located typically within the body 114 of the handpiece 110. It is appreciated that the motor drive 136 may include a motor gearing 134 and a cam drive 170, and may extend generally longitudinally along a body axis 118 of the handpiece 110. Connected to the motor drive 136 is the motor gearing 134, which is in engagement with the tool gearing 132 for rotating the cam follower 124 and the tool removably secured therein (not shown). The motor gearing 134 may be located at a free end of the motor drive 136 (extending generally radially from the body axis 118) at a connection opening between the head portion 112 and the handpiece body 114 of the handpiece 110.

The cam follower 124 may further include an outer groove 144 (e.g., extending along perimeter of the cam follower 124 in a transverse direction to the head axis 128. The outer groove 144 may include a top wall 144a, a bottom wall 144b, and a base surface 144c extending therebetween, and being dimensioned to receive a free end 172 of the cam drive 170 of the motor drive 136. Desirably, the cam drive 170 extends longitudinally from the free end 174 of the motor drive 136 and/or the motor gearing 134 along an offset axis 175 relative to (and generally parallel to) the body axis 118. As the motor drive 136 rotates about the body axis 118, the cam drive 170 located at the end of the motor drive 136 revolves (e.g., orbits) the body axis 118 along a displaced path (e.g., a concentric path). The motor gearing 134 and/or the motor drive 136 may include a drive pin 176 in communication with the cam drive 170. The cam drive may be free to rotate about the drive pin 176 (i.e., and about the offset axis), though not required. Furthermore, the cam drive 170 may include an outer surface 177 having at least one flat surface 178 and preferably at least two flat surfaces. In one specific example, the cam drive 170 may include an upper flat surface 178a and a bottom flat surface 178b. Desirably, the vertical spacing (e.g., the base surface 144c) between the top tall 144a and the bottom wall 144c of the outer groove 144 is dimensioned relative to the vertical distance between the upper and bottom surfaces 178a and 178b to prevent the cam drive 170 from rotating within the groove 144 while allowing the drive pin 176 to rotate within the cam bore 180. Alternatively, the cam drive 170 may be fixedly secured to the drive pin 176 thereby preventing the rotation of the drive pin 176 with the cam bore 180. In this configuration, the drive pin 176 may be capable of freely rotating within motor gearing 134 and/or the motor drive 136. It is appreciated that the cam drive 170 and the respective outer groove 144 may be provided in various shapes and/or sizes.

As discussed above, the cam drive 170 may include two opposing flat surfaces 178a,178b that define a width W therebetween, the width W corresponding to the distance (e.g., height) between the opposing spaced apart walls 144a and 144b of the groove 144. It is appreciated that a distance X may be provided which defines a radial distance between the body axis 118 and the offset axis 175 such that the flat surface(s) 178 may include a length L (e.g., the distance transverse to the offset axis and the width W of cam drive 170) having a distance of at least about 1/16, preferably at least about 1/8, and more preferably at least about 1/4 of the distance X. Furthermore, the flat surface 178 of the cam drive 170 may include a length L having a distance less than about 5 times, preferably less than 4 times, and more preferably less than about 3 times (e.g., about 2 times) of the distance X. For example, the flat surface 178 may include a length having a distance ranging from about 1/16 to about 5 times, preferably from about 1/8 to about 4 times, and more preferably about % to about 3 times (e.g., about 2 times) of the distance X.

It is appreciated that X may be at least about 0.25 mm, and preferably at least about 0.5 mm. Furthermore, it is appreciated that X may be less than about 2.25 mm and preferably less than about 1.5 mm. For example, X may range from about 0.25 mm to about 2.25 mm, and preferably about 0.5 mm to about 1.5 mm. In doing so, it is believed that the vertical movement (e.g., vertical oscillation) of the cam follower (and the tool secured thereto) may range from about 0.5 mm to about 4.5 mm, and preferably about 1 mm to about 3 mm along the head axis 138.

The motor gearing 134 is in engagement with the tool gearing 132 to adjust the direction of rotation from along the body axis 118 to the head axis 128 (e.g., from greater than 0 to less than 180 degrees such as about 90 degrees). In doing so, rotational power from the motor (not shown) is transferred along the motor drive about the body axis 118 through the motor gearing 134 to the cam follower 134 through the tool gearing 132. The tool gearing 132 (being generally perpendicular to the motor gearing 132) transfers the rotational power about the head axis 128 to the tool housing (not shown) within the cam follower 134 for rotation of the tool (not shown) removable secured therein.

As the motor drive 136 rotates, the cam drive 170 moves along the displaced path (e.g., concentric path, which may be radially displaced from the body axis 118). Desirably, the cam drive 170 may be free to rotate about the drive pin 170 (e.g., and the offset axis) at the free end 174 of the motor drive 136 and/or the motor gearing 134, which allows the cam drive 170 and more specifically the opposing flat surfaces 178 of the cam drive 170 to generally maintain their rotational position relative to the offset axis 175 as the cam drive 170 revolves around the body axis 118. In doing so, the top flat surface 178a and the bottom top surface 178b remain generally juxtaposed to the respective top and bottom walls 144a and 144b of the groove 144 while allowing the cam drive 176 to slide laterally (e.g., side to side such as transversely to the head axis 128 and the body axis 118) within the groove 144.

More particularly, as the cam drive 170 continues to revolve around the body axis 118 and along the displaced path (e.g., at the radial distance X from the body axis 118), it urges the cam follower 124 generally vertically (e.g., up or down along the head axis 128) while sliding laterally (e.g., left or right) within the groove 144 to substantially minimize or prevent lateral movement of the cam follower 124 from head axis 128 (and/or prevent rotational movement of the cam follower 124 about the body axis 118). Therefore, the cam drive 170 engages with the cam follower 124 thus causing the tool housing to oscillate vertically in an up and down motion (relative to the body axis 118) while rotating as well. The tool is connected to the cam follower 124, which then causes the tool to rotate as it is vertically oscillating in an up and down manner.

It is appreciated that a face width of the tool gearing 132 may include a length FW that corresponds to the vertical distance (e.g., about two times the radial distance X) traveled by the cam follower 124 during oscillation. This allows the tool gearing 132 to remain in engagement with the motor gearing 134 during at least part of an oscillation cycle and preferably throughout an entire oscillation cycle (e.g., maximum elevation of the tool to the minimum elevation of the tool). More particularly, it is contemplated that the cam follower 124 may be moved (e.g., oscillated) an oscillation distance Y or stroke (e.g., about two times the radial distance X) that defines a distance (e.g., vertical distance) between a maximum elevation of the cam follower 124 (e.g., tool housing and/or tool) as shown in FIGS. 7-8 and 11A-11B to a minimum elevation of the cam follower 124 as shown in FIGS. 9-10 and 12A-12B such that the tool gearing 132 may include a face width having a length FW with a distance of at least about 1/16, preferably at least about 1/8, and more preferably at least about 1/4 of the oscillation distance Y. Furthermore, the face width may include a length FW having a distance less than about 5 times, preferably less than 4 times, and more preferably less than about 3 times (e.g., about 2 times) of the oscillation distance Y. For example, the face width of the tool gearing 132 may include a length FW having a distance ranging from about 1/16 to about 5 times, preferably from about 1/8 to about 4 times, and more preferably about 1/4 to about 3 times (e.g., about 2 times) of the oscillation distance Y.

Figure 13A:
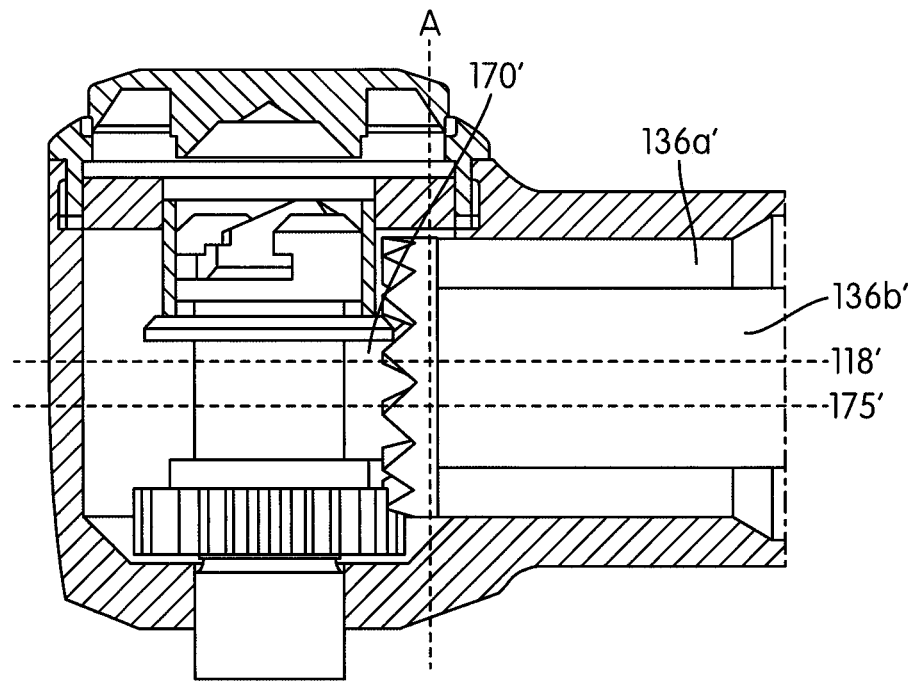
FIG. 13A is a side view of a portion of another multi-directional handpiece assembly in accordance with embodiments of the present invention.
Figure 13B:
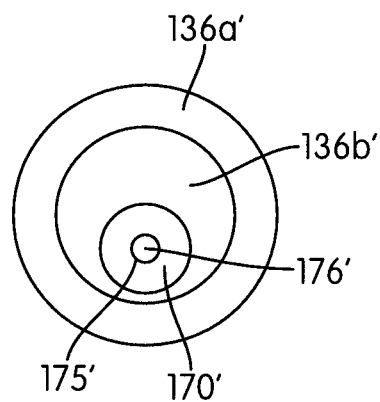
FIG. 13B is a front cross-sectional view of the multi-directional handpiece shown in FIG. 13A taken across A-A.

In an alternative embodiment of the multi-directional handpiece may include at least two different drive shafts 136' to drive the axial displacement (vertical oscillation) and the rotation. As shown in FIG. 13A-13B, the multi-directional handpiece 110' includes a first motor drive 136a' for driving the rotation of the tool and a second motor drive 136b' for driving the rotation of the cam drive 170' thereby driving the oscillation of the tool. In this configuration the handpiece 110' may further include a first motor (not shown) coupled to and for driving the first motor drive 136a' and a second motor (not shown) coupled to and for driving the second motor drive 136b'. Optionally, the second motor drive 136b' may further include a drive pin 176' in communication with the cam drive 170' to allow for free rotation of the cam drive 170' radially from the an offset axis 175'. In one specific example, the first motor is a small motor for rotation of the tool, which would produce little or almost no torque at slower speeds (e.g., around about 20-50/min (rpms)) and the second motor being a larger motor to drive the oscillation of the tool (along the head axis) to produce larger force (e.g., torque). Desirably, this would enable an adjustment of the speeds of these 2 different frequencies (dynamic adjustment or with presets upon the canal type) and/or would allow a better monitoring of the rotational torque because each shaft is dedicated to do only one task (e.g., rotation of the tool or oscillation of the tool).

The invention described herein has many other advantages. The endodontic instrument may have a single continuous flow path, which eliminates potential leak paths. Inherent stress concentrations may be reduced or substantially eliminated, thereby allowing the tip and/or the distal end portions to be reliable during vibration. The configuration of the tip and/or the distal end portions guide and transfer the ultrasonic vibration and energy in the planes of motion, which provides proper agitation to the irrigants. The tip assembly can also be disposable, thereby requiring that a new tip assembly be used for each patient and insuring that the tip assembly will be sterile prior to use.

Each feature disclosed in this specification (including any accompanying claims, abstract, and drawings), may be replaced by alternative features having the same, equivalent or similar purpose, unless expressly stated otherwise. Thus, unless expressly stated otherwise, each feature disclosed is one example only of a generic series of equivalent or similar features.

While preferred embodiments of the present invention have been shown and described herein, it will be obvious to those skilled in the art that such embodiments are provided by way of example only. Numerous variations, changes, and substitutions will be apparent to those skilled in the art without departing from the invention. Other foreseen embodiments or uses for the present invention include the use of the invention in the field of phacoemulsification, where a tip assembly such as the present invention may offer many advantages. Accordingly, it is intended that the invention be limited only by the scope of the appended claims.

The invention claimed is:

1. A multi-directional handpiece comprising:
   a motor drive extending along and configured for rotation about a body axis, the motor drive having:
   a motor gearing at a proximal end of the motor drive; and
   a rotatable cam drive at the proximal end of the motor drive, the rotatable cam drive extending along an offset axis and being generally parallel to the body axis; and
   a cam follower extending along a head axis; the cam follower having:
   a groove having opposing spaced apart walls for receiving the cam drive;
   a file gearing in engagement with the motor gearing for transferring the rotational movement of the motor drive about the body axis to the cam follower about the head axis; and
   a housing for a workpiece; and
   wherein through rotation of the motor drive, the rotatable cam drive rotates about the offset axis while revolving around the body axis thereby moving the cam follower generally along the head axis so that the workpiece moves in an oscillating motion while being rotated.

2. The multi-directional handpiece of claim 1, wherein the workpiece is axially oscillated from 1 to 20 times for every revolution.

3. The multi-directional handpiece of claim 1, wherein the workpiece is axially oscillated from 1 to 10 times for every revolution.

4. The multi-directional handpiece of claim 1, wherein the workpiece is axially oscillated at least 1 time for every revolution.

5. The multi-directional handpiece of claim 1, wherein the workpiece is axially oscillated at least 2 times for every revolution.

6. The multi-directional handpiece of claim 1, wherein the workpiece is axially oscillated less than 10 times for every revolution.

7. The multi-directional handpiece of claim 1, wherein the workpiece is axially oscillated less than 7 times for every revolution.

8. The multi-directional handpiece of claim 1, wherein the workpiece is rotated either clockwise, counterclockwise or in reciprocation.

9. The multi-directional handpiece of claim 1, wherein the workpiece is a file.

* * * * *